US009982967B2

United States Patent
Singletary et al.

(10) Patent No.: US 9,982,967 B2
(45) Date of Patent: May 29, 2018

(54) COMPOSITE BALLISTIC RESISTANT LAMINATE

(71) Applicant: E I DU PONT DE NEMOURS AND COMPANY, Wilmington, DE (US)

(72) Inventors: James Neal Singletary, Midlothian, VA (US); Leopoldo Alejandro Carbajal, Newark, DE (US); William George Kampert, Wilmington, DE (US); Timothy A Libert, Hockessin, DE (US); Bryan Benedict Sauer, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 135 days.

(21) Appl. No.: 14/709,627

(22) Filed: May 12, 2015

(65) Prior Publication Data
US 2016/0265882 A1 Sep. 15, 2016

Related U.S. Application Data

(63) Continuation-in-part of application No. 14/625,193, filed on Feb. 18, 2015, now abandoned.

(51) Int. Cl.
*B32B 7/02* (2006.01)
*F41H 5/04* (2006.01)
(Continued)

(52) U.S. Cl.
CPC ............... *F41H 5/04* (2013.01); *B32B 5/02* (2013.01); *B32B 5/12* (2013.01); *B32B 7/00* (2013.01);
(Continued)

(58) Field of Classification Search
CPC ............ B32B 2250/00; B32B 2250/05; B32B 2250/40; B32B 2255/02; B32B 2255/10;
(Continued)

(56) References Cited

U.S. PATENT DOCUMENTS

| 4,309,487 A | 1/1982 | Holmes |
| 6,689,412 B1 | 2/2004 | Bourrieres |

(Continued)

FOREIGN PATENT DOCUMENTS

WO  2015/022234 A1  2/2015

OTHER PUBLICATIONS

International Search Report, dated Dec. 15, 2016, for International Application PCT/US2016/032699, filed on May 16, 2016, ISA European Patent Office, Jan Boon, authorized officer.

*Primary Examiner* — Lawrence Ferguson

(57) ABSTRACT

An impact penetration resistant laminate comprises a plurality of alternating layers of (i) non-fibrous ultra-high molecular weight polyethylene monolayers and (ii) a thermoplastic adhesive, the adhesive having a basis weight of no greater than 5 gsm and a zero-shear-rate viscosity, determined from an oscillating disc rheometer in a frequency sweep between 0.1 rad/s and 100 rad/s, conducted per ASTM D 4440 at 125° C., and calculated from fitting to a Carrea-Yasuda four parameter model, of at least 1500 Pa-s, wherein
(a) at least 90 percent of the monolayers are arranged such that the orientation of one monolayer is offset with respect to the orientation of an adjacent monolayer, and
(b) the modulus of elasticity through the thickness of the laminate is at least 3 GPa.

9 Claims, 1 Drawing Sheet

(51) Int. Cl.
| | |
|---|---|
| B32B 5/12 | (2006.01) |
| B32B 7/00 | (2006.01) |
| B32B 7/12 | (2006.01) |
| B32B 27/08 | (2006.01) |
| B32B 27/32 | (2006.01) |
| B32B 7/04 | (2006.01) |
| B32B 27/06 | (2006.01) |
| B32B 27/18 | (2006.01) |
| B32B 27/20 | (2006.01) |
| B32B 37/06 | (2006.01) |
| B32B 37/08 | (2006.01) |
| B32B 37/10 | (2006.01) |
| B32B 37/12 | (2006.01) |
| G01N 3/30 | (2006.01) |
| B32B 5/02 | (2006.01) |
| B32B 27/12 | (2006.01) |

(52) U.S. Cl.
CPC ............ *B32B 7/005* (2013.01); *B32B 7/02* (2013.01); *B32B 7/04* (2013.01); *B32B 7/12* (2013.01); *B32B 27/06* (2013.01); *B32B 27/08* (2013.01); *B32B 27/12* (2013.01); *B32B 27/18* (2013.01); *B32B 27/20* (2013.01); *B32B 27/32* (2013.01); *B32B 37/06* (2013.01); *B32B 37/08* (2013.01); *B32B 37/10* (2013.01); *B32B 37/12* (2013.01); *F41H 5/0478* (2013.01); *G01N 3/30* (2013.01); *B32B 2250/00* (2013.01); *B32B 2250/05* (2013.01); *B32B 2250/40* (2013.01); *B32B 2250/42* (2013.01); *B32B 2255/02* (2013.01); *B32B 2255/10* (2013.01); *B32B 2255/26* (2013.01); *B32B 2262/0253* (2013.01); *B32B 2264/00* (2013.01); *B32B 2264/02* (2013.01); *B32B 2264/10* (2013.01); *B32B 2307/51* (2013.01); *B32B 2307/514* (2013.01); *B32B 2307/516* (2013.01); *B32B 2307/542* (2013.01); *B32B 2307/558* (2013.01); *B32B 2307/581* (2013.01); *B32B 2307/732* (2013.01); *B32B 2307/734* (2013.01); *B32B 2309/02* (2013.01); *B32B 2309/04* (2013.01); *B32B 2309/12* (2013.01); *B32B 2323/04* (2013.01); *B32B 2571/00* (2013.01); *B32B 2571/02* (2013.01); *G01N 2203/001* (2013.01); *G01N 2203/0232* (2013.01)

(58) Field of Classification Search
CPC ........ B32B 2255/26; B32B 2262/0253; B32B 2264/00; B32B 2264/02; B32B 2264/10; B32B 2307/51; B32B 2307/514; B32B 2307/542
See application file for complete search history.

(56) References Cited

U.S. PATENT DOCUMENTS

| | | |
|---|---|---|
| 7,923,094 B1 | 4/2011 | Harding et al. |
| 7,972,679 B1 | 7/2011 | Lyons et al. |
| 7,976,932 B1 | 7/2011 | Lyons et al. |
| 7,993,715 B2 | 8/2011 | Geva et al. |
| 8,197,935 B2 | 6/2012 | Bovenschen et al. |
| 2006/0047046 A1* | 3/2006 | Haas ................ B82Y 30/00 524/432 |
| 2006/0051577 A1 | 3/2006 | Tam et al. |
| 2011/0083415 A1 | 4/2011 | Marissen et al. |
| 2011/0266710 A1 | 11/2011 | Tam et al. |
| 2012/0207966 A1 | 8/2012 | Dickson |

\* cited by examiner

COMPOSITE BALLISTIC RESISTANT LAMINATE

RELATED APPLICATION

This application is a continuation-in-part of application Ser. No. 14/625,193 filed on Feb. 18, 2015.

BACKGROUND

1. Field of the Invention

This invention pertains to an impact penetration resistant laminate suitable for use in hard armor.

2. Description of Related Art

U.S. Pat. No. 4,309,487 to Holmes describes a laminated armor structure consisting of one or more plies of unidirectionally oriented polyethylene film or fibers which are positioned so that the lines of orientation of adjacent units are at angles to each other. Bonding of the plies is achieved solely through the application of heat and pressure to the composite of positioned plies.

U.S. Pat. No. 7,972,679 to Lyons et al discloses a ballistic-resistant molded article having a sandwich-type structure including two outer portions of a first high modulus material surrounding an inner portion of a second high modulus material. The outer portions are comprised of a plurality of interleaved layers of adhesive coated cross-plied non-fibrous ultra-high molecular weight polyethylene tape. The inner portion is comprised of a plurality of interleaved layers of high modulus cross-plied fibers embedded in resin. The stack of interleaved layers is compressed at high temperature and pressure to form a hybrid sandwich ballistic-resistant molded article that includes a mix of high modulus materials. It has been found that ballistic resistance is higher for the hybrid structure than for a monolithic structure of comparable areal density.

U.S. Pat. No. 7,976,932 to Lyons et al teaches a ballistic resistant panel including a strike face portion and a backing portion. The strike face portion includes a plurality of interleaved layers of non-fibrous ultra-high molecular weight polyethylene tape. The backing portion includes a plurality of interleaved layers of cross-plied fibers of ultra-high molecular weight polyethylene. The entire stack of interleaved layers is compressed at high temperature and pressure to form a ballistic resistant panel having a strike face on one side. It was been found that ballistic resistance increases as the weight ratio of the strike face portion with respect to the backing portion decreases. A composite panel having a strike face of Tensylon® tape with at most 40% of the total weight of the panel exhibits improved ballistic resistance properties as compared to a monolithic structure of strictly interleaved layers of cross-plied high modulus fibers.

U.S. Pat. No. 8,197,935 to Bovenschen at al discloses a ballistic-resistant moulded article having a compressed stack of sheets including reinforcing elongate bodies, where at least some of the elongate bodies are polyethylene elongate bodies that have a weight average molecular weight of at least 100,000 gram/mole and a Mw/Mn ratio of at most 6.

U.S. Pat. No. 7,993,715 to Geva at al relates to polyethylene material that has a plurality of unidirectionally oriented polyethylene monolayers cross-plied and compressed at an angle to one another, each polyethylene monolayer composed of ultra-high molecular weight polyethylene and essentially devoid of resin. The invention further relates to ballistic resistant articles that include or incorporate the inventive polyethylene material and to methods of preparing the material and articles incorporating same.

SUMMARY OF THE INVENTION

This invention pertains to a consolidated impact penetration resistant laminate comprising a plurality of alternating layers of (i) non-fibrous ultra-high molecular weight polyethylene monolayers and (ii) a thermoplastic adhesive, the adhesive having a basis weight of no greater than 5 gsm and a zero-shear-rate viscosity, determined from an oscillating disc rheometer in a frequency sweep between 0.1 rad/s and 100 rad/s, conducted per ASTM D 4440 at 125° C., and calculated from fitting to a Carrea-Yasuda four parameter model, of at least 1500 Pa-s, wherein (a) at least 90 percent of the monolayers are arranged such that the orientation of one monolayer is offset with respect to the orientation of an adjacent monolayer, and (b) the modulus of elasticity through the thickness of the thickness of the laminate, as measured by Test Method A, is at least 3 GPa.

The invention further pertains to a method of making an impact penetration resistant laminate comprising the steps of (i) providing a plurality of cross-plied non-fibrous ultra-high molecular weight polyethylene sheets wherein the polyethylene sheet comprises two monolayers of polyethylene oriented film separated by an adhesive arranged such that the orientation of one monolayer in the sheet is offset with respect to the orientation of the other monolayer in the sheet, wherein the adhesive has a basis weight of no greater than 5 gsm and a zero-shear-rate viscosity, determined from an oscillating disc rheometer in a frequency sweep between 0.1 rad/s and 100 rad/s, conducted per ASTM D 4440 at 125° C., and calculated from fitting to a Carrea-Yasuda four parameter model, of at least 1500 Pa-s, (ii) assembling a stack comprising a plurality of UHMWPE sheets of step (i) in an arrangement wherein at least 90 percent of the sheets are positioned such that the orientation of a monolayer of one sheet is offset with respect to the orientation of the closest monolayer of an adjacent sheet and the combined weight of polyethylene sheets and adhesive in the stack is from 0.6-600 kg/m$^2$, (iii) subjecting the stack of step (ii) to a pressure of from 10 to 400 bar and a temperature of from 70 to 150 degrees C. for between 5 and 60 minutes, and (iv) cooling the laminate to a temperature of 50 degrees C. or less.

For practical reasons, the laminate is assembled from a plurality of cross-piled sheets.

DETAILED DESCRIPTION

The date and/or issue of specifications referenced in this section are as follows:

ASTM D 7744-11, "Standard Test Method for Tensile Testing of High Performance Polyethylene Tapes". Published September 2011.

ASTM D 4440-07, "Standard Test Method for Plastics: Dynamic Mechanical Properties: Melt Rheology". Published March 2007.

Cross-Plied Sheet

Figure 1:
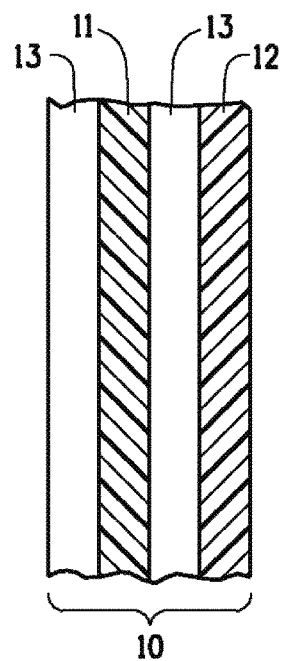
FIG. 1 shows a cross section through a cross-plied non-fibrous ultra-high molecular weight (UHMWPE) polyethylene sheet.

A cross-pied sheet is shown at 10 in FIG. 1 and comprises two monolayers of ultra-high molecular weight (polyethylene (UHMWPE) oriented film 11 and 12 and two layers of adhesive 13. By UHMWPE is meant a film made from a polyethylene polymer having a viscosity average molecular weight of at least 2 million. In some embodiments the molecular weight is between 2-6 million or even 3-5 million. More preferably the viscosity average molecular weight at least 4 million. Examples of suitable polyethylene materials are Ticona GUR from Ticona Engineering Polymers, Auburn Hills, Mich. and Hi-ZEX MILLION™ from Mitsui Chemicals America, Inc., Rye Brook, N.Y.

Each film monolayer is non-filamentary and is highly oriented. By highly oriented is meant that the modulus in one direction, normally the direction in which the oriented film monolayer is produced, is at least 10 times greater than in any other direction. Preferably, the modulus in one direction is at least 20 times greater and more preferably at least 30 times greater than in any other direction The two oriented film monolayers 11 and 12 in FIG. 1 are combined with an adhesive 13 to form a cross-plied sheet 10 in which the orientation of one oriented film monolayer 11 is offset with respect to the orientation of the other oriented film monolayer 12. Preferably the two oriented film monolayers layers 11 and 12 have an orientation that is essentially orthogonal to each other. By "essentially orthogonal" is meant that the two sheets are positioned relative to each other at an angle of 90+/−15 degrees. This is sometimes referred to as a 0/90 arrangement.

Two thermoplastic adhesive layers 13 are positioned a shown in FIG. 1. The cross-piled sheet 10 described above comprises two monolayers and two adhesive layers. This is a preferred construction, however a sheet may comprise more than two monolayers or more than two adhesive layers such as in a 0/90/0/90 arrangement.

The term "film" as used herein refers to UHMWPE products having widths on the order of at least 10 mm or greater, preferably greater than about 20 mm, more preferably greater than about 30 mm and even more preferably greater than about 40 mm of a generally rectangular cross-section and having smooth edges and is specifically used to distinguish from the "fibrous" UHMWPE products that are on the order of 3 mm wide or narrower. The UHMWPE film of the present invention includes a width of at least about 25 mm, a thickness of between 0.038 mm and 0.102 mm, and a first modulus, defined as "Ml" in ASTM D7744, of at least about 100 N/Tex, preferably at least about 120 N/Tex, more preferably at least about 140 N/Tex, and most preferably at least about 160 N/Tex. In some embodiments, the film has a very high width to thickness ratio, unlike fibrous UHMWPE, which has a width that is substantially similar to the thickness. A UHMWPE film according to the present invention, for example, may include a width of 25.4 mm and a thickness of 0.0635 mm, which indicates a width to thickness ratio of 400:1. The film may be produced at a linear density of from about 660 Tex to about 1100 Tex and higher. There is no theoretical limit to the width of the high modulus polyethylene film, and it is limited only by the size of the processing equipment. The cross-pied sheet as used herein is meant to refer to thin sections of material in widths greater than about 0.2 m and up to or exceeding 1.6 m width as could be produced in large commercial equipment specifically designed for production in such widths and having a rectangular cross-section and smooth edges.

Adhesive

A thermoplastic adhesive 13 in FIG. 1 is placed adjacent to the surface of each monolayer to bond adjacent monolayers together. Each adhesive layer has a basis weight of no greater than 5 gsm and a zero-shear-rate viscosity, when measured at 125° C. by an oscillating disc rheometer, of at least 1500 Pa-s. In some embodiments, the adhesive has a zero-shear-rate viscosity of at least 10,000 Pa-s. In yet other embodiments, the adhesive has a zero-shear-rate viscosity of at least 100,000 Pa-s. In other embodiments, the adhesive has a zero-shear-rate viscosity of at least 1,000,000 Pa-s.

Zero-shear-rate viscosity can be determined by measuring the complex viscosity of an adhesive sample per ASTM D 4440. The adhesive is held at 125° C. in an oscillating disc rheometer, and subjected to oscillation across a frequency sweep from 0.1 rad/s to 100 rad/s. Viscosity as a function of frequency is then fitted to the so-called four parameter Carreau-Yasuda equation:

$$\eta = (\eta_{o,cy})/[1+(\tau_{cy}\gamma')^a]^{p/a}$$

where $\eta_{o,cy}$ is the Carreau-Yasuda zero-shear-rate viscosity, $\tau_{cy}$ is the Carreau-Yasuda time constant, p is the Carreau-Yasuda rate constant that describes the slope of the power-law region, and a is the parameter that describes the transition region between the Newtonian region and the power-law region. Multiple frequency sweeps should be performed and averaged before fitting the data to the equation to determine the zero-shear-rate viscosity. Such measurements are known to one skilled in the art of polymer characterization. A suitable rheometer has been found to be an ARES LS2 from TA Instruments, New Castle, Del. A forced convection oven has been found adequate for controlling the adhesive sample temperature. Using this equipment, plate temperature can be calibrated using a disc of perfluoroalkoxy polymer with a thermocouple in the middle. 25 mm diameter plates with smooth surfaces are used for mounting the adhesive sample. Adhesive samples may be variously cast or machined to form the cylindrical sample needed to contact the oscillating plates, depending on the nature of the adhesive. Care should be taken to avoid degrading the adhesive during specimen preparation. An exemplary description of the application of the Carreau-Yasuda model to polymer flow is given in Stephen L. Rosen, Fundamental Principles of Polymeric Materials, John Wiley & Sons, New York, 1982, page 207.

In some embodiments the weight of the adhesive layer is less than 4.5 gsm or even less than 4 gsm.

Suitable examples of adhesive are urethanes, polyethylene, ethylene copolymers including ethylene-octene copolymers, ionomers, metallocenes, and thermoplastic rubbers such as block copolymers of styrene and isoprene or styrene and butadiene. The adhesive may further comprise a thixotrope to reduce the propensity for adjacent sheets to slide relative to each other during a compression process. Suitable thixotropes include organic particles whose shape can be characterized as dendritic (representative of which is DuPont™ Kevlar® aramid fiber pulp), spherical, plate-like, or rod-like, or inorganic particles such as silica or aluminum trihydrate. The adhesive may further include other functional additives such as nanomaterials and flame retardants.

The adhesive may be in the form of a film, paste, liquid or nonwoven scrim.

Impact Penetration Resistant Laminate

Figure 2:
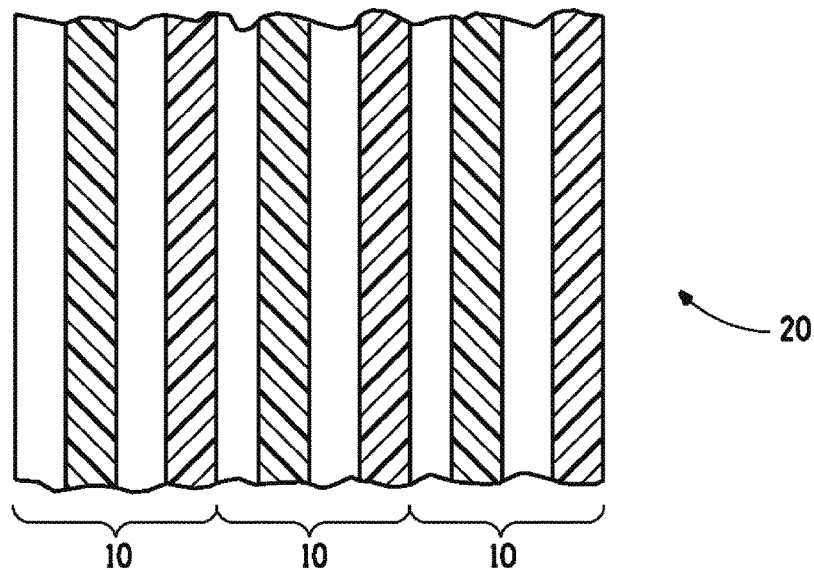
FIG. 2 shows a cross section through a laminate comprising a plurality of cross-plied sheets.

FIG. 2 shows an exemplary laminate comprising a plurality of cross-pied non-fibrous ultra-high molecular weight polyethylene sheets 10. In some embodiments, at least 90 percent, more preferably at least 95 percent or most preferably 100 percent of the sheets are positioned within the laminate such that the orientation of a monolayer of one polyethylene sheet is offset with respect to the orientation of the closest monolayer of an adjacent sheet.

The number of polyethylene sheets in a laminate will vary based on the design requirements of the finished article but typically is in the range of from 20 to 1000 giving a laminate weight range of from 0.1 to 600 kg/m² or from 1 to 60 kg/m² or even from 1 to 40 kg/m². The laminate is formed by compression of a stack of sheets at a temperature at which the adhesive will flow but is less than the temperature at which the monolayer of the sheet loses orientation, and thus mechanical strength. Typically the adhesive comprises no more than 15 weight percent of the combined weight of polyethylene sheet plus adhesive in the laminate.

The modulus of elasticity through the thickness of the compressed laminate, as measured by Test Method A, is at least 3 GPa, In some embodiments, the modulus of elasticity is at least 3.2 GPa or even at least 3.5 GPa. In another embodiment, the modulus of elasticity is at least 4 GPa. Preferably, the modulus of elasticity through the thickness of the compressed laminate should be no higher than ten times the modulus of elasticity through the thickness of the polyethylene sheet component of the laminate.

A method of making an impact penetration resistant laminate comprises the steps of (i) providing a plurality of cross-plied non-fibrous ultra-high molecular weight polyethylene sheets 10 wherein the polyethylene sheet comprises two monolayers of polyethylene oriented film 11 and 12 separated by an adhesive 13 arranged such that the orientation of one monolayer 11 is offset with respect to the orientation of the other monolayer 12, wherein the adhesive has a basis weight of no greater than 5 gsm and a zero-shear-rate viscosity, when measured per ASTM D 4440 at 125° C. in a frequency sweep between 0.1 rad/s and 100 rad/s by an oscillating disc rheometer, and fitted to the four parameter Carreau-Yasuda model, of at least 1500 Pa-s, (ii) assembling a stack 20 comprising a plurality of UHMWPE sheets 10 of step (i) in an arrangement wherein at least 90 percent of the sheets are positioned such that the orientation of a monolayer of one sheet is offset with respect to the orientation of the closest monolayer of an adjacent sheet and the combined weight of polyethylene sheets and adhesive in the stack is from 0.6 to 600 kg/m², (iii) subjecting the stack of step (ii) to a pressure of from 10 to 400 bar and a temperature of from 70 to 150 degrees C. for between 5 and 60 minutes, and (iv) cooling the laminate to a temperature of 25 degrees C. or less.

Preferably, the stack is assembled in such a manner that the stack comprises alternating layers of monolayer 11 or 12 and adhesive 13.

In some embodiments, the combined weight of polyethylene sheets and adhesive in the stack of step (ii) is from 1 to 40 kg/m², Under the processing conditions described above, it has been surprisingly found that the impact penetration resistance of the compressed laminate increased at molding temperatures higher than previously taught.

TEST METHODS

Test Method A

The modulus of elasticity ($E_3$) through the thickness of a compressed laminate was determined using the speed of sound through the thickness of the part, $C_{33}$. $C_{33}$ may be determined by a low pressure contacting ultrasonic speed of sound measurement. A suitable measuring device is an Opus 3-D thickness transmission instrument from SoniSys, Atlanta, Ga., at default settings. It requires input of the sample areal density, AD, then automatically determines thickness, t, and $C_{33}$ in through thickness transmission at 1-MHz frequency. One skilled in the art could use other devices.

From the measured $C_{33}$ and the density of the part, $\rho$, $E_3$ is calculated as: $E_3 = [C_{33} \, t/AD]^{1/2}$ Test Method B This method provides a means to assess whether a consolidated stack of cross-pied non-fibrous ultra-high molecular weight polyethylene sheets will or will not suffer a pressure loss greater than 35 bar within the first two minutes and/or greater than 70 bar within the first 5 minutes when subjected to a compaction at a pressure of 255 Bar and a temperature of 132 degrees C.

Polyethylene sheets as previously described are cut into 50 mm×50 mm squares such that one of the monolayers comprising the sheet is cut in the direction of high orientation. The second monolayer comprising the sheet is orthogonal to the first layer. A stack of sheets (20 in FIG. 2) is assembled such that the sheets are positioned within the stack such that the orientation of a monolayer of one polyethylene sheet is offset at an angle of 90 degrees with respect to the orientation of the closest monolayer of the adjacent polyethylene sheet. The stack should have an areal density of 660+/−50 gsm.

Test Method B requires a press with highly parallel, heated platens, which can be pressurized manually and indicate pressure over time. An example of a suitable press is a Two Post Press Model C from Carver, Inc., Wabash, Ind. The press platens are preheated to 132° C. The pre-prepared stack sample is placed between a layer of thin, heat tolerant release material that will not adhere to the sample or allow adhesive from the sample to flow and foul the platens. Exemplary release material is polyimide film available from E. I. du Pont de Nemours and Company (hereinafter "DuPont"), Wilmington, Del. under the tradename Kapton. The sample is placed in the center of the platen, and a pressure of about 255-Bar applied to the sample based on its original 50 mm×50 mm dimensions. The pressure is monitored every minute for five minutes. The pressure is released and the sample removed. The procedure is repeated except that no stack is present and the pressure is monitored for five minutes. Only the release material is between the platens. This measurement gives an indication of the compliance of the press. A plot of the absolute value of the difference between the two pressure versus time curves, shows the compliance of the test material. It has been discovered that samples which show a material compliance of less than about 35-Bar pressure loss after two minutes and/or less than about 70-Bar pressure loss after five minutes, are unlikely to have sheet slip relative to each other during large scale manufacturing of the laminates and thus provide a laminate having a modulus of elasticity through the thickness of the laminate, as measured by Test Method A, of at least 3 GPa.

All ballistic targets were shot backed by an approximately 13 cm thick block of plastilina modeling clay following the "V50" test protocol described in MIL-STD-662F, issued 18 Dec. 1997. V50 is a statistical measure that identifies the average velocity at which a bullet or a fragment penetrates the armor equipment in 50% of the shots, versus non penetration of the other 50%. The parameter measured is V50 at zero degrees where the degree angle refers to the obliquity of the projectile to the target.

EXAMPLES

In all examples, the sheet material comprised two monolayers of UHMWPE cross-plied in a 0/90 degree orientation and two layers of adhesive such that each mono layer and each adhesive layer are arranged alternatively. The monolayer material was Tensylon™ HS grade oriented film obtainable from E. I. DuPont de Nemours and Company, Wilmington, Del. The sheet material had a nominal areal weight of 50 gsm. The sheets were cut into 500 mm×500 mm squares such that one of the monolayers comprising the sheet was cut in the direction of highest orientation.

Comparative Example Series A

In this series of examples, a plurality of stacks with each stack comprising forty sheets of Tensylon® HS were assembled such that the orientation of a monolayer of one sheet is offset with respect to the orientation of the nearest monolayer of an adjacent sheet. The adhesive used in the sheet was a spunbonded 6 gsm nonwoven scrim of low linear density polyethylene. The scrim was style PO4605 from Spunfab Ltd., Cuyahoga Falls, Ohio having a zero-shear-rate viscosity at 125° C. of 1310 Pa-s. The stack was placed between flat parallel hard steel platens in a model C Carver Press between thin release films of DuPont™ Kapton® polyimide, and compressed to a pressure of 10 bar. The temperature was then raised to the desired platen temperature at which temperature there was a compression dwell of five minutes. Following this dwell, the pressure was increased with the intent of obtaining a pressure of 204 bar within about 20 seconds. If the targeted 204 bar pressure was reached, the stack was held under pressure for five minutes, then cooled, while still under pressure, to less than 40° C. platen temperature before being released from pressure.

A laminate molded at a platen temperature of 100° C. did not change dimensions. A laminate molded at a platen temperature of 110° C. spread laterally to slightly larger dimensions, but was still generally square. A laminate molded at a platen temperature of 116° C. slipped in the mold before reaching maximum pressure, resulting in a part that lost its intended reinforcement position and orientation, thus resulting in a ruined part. Before reaching maximum pressure, a laminate molded at a platen temperature of 121° C. slipped so far in the mold that the final location of some of the sheet layers did not intersect with their original locations, resulting in a ruined part with the further possibility of damage to the molding equipment or injury to operators, depending on the press and safety containment around it.

These comparative experiments show that the UHMWPE sheet laminate articles taught in U.S. Pat. No. 7,972,679 cannot be consistently, correctly or safely made at a combination of high temperature and pressure using equipment commonly used for making polyethylene laminates. This explains why previous teachings, like U.S. Pat. No. 7,972,679, used either molding temperatures below about 121° C., or molding pressures below about 100 bar, as the combination of high temperature and pressure tends to make an oriented polyethylene oriented film-reinforced composite unstable under high transverse temperature and pressure, dissuading one skilled in the art from attempting to manufacture them.

Examples to Derive a Regression Curve

Laminates were made in a similar manner to those of Comparative Example Series A except that each stack comprised only 20 sheets. This lower number of sheets is adequate to provide information to generate a regression curve. Laminates were molded at a maximum pressure of 10, 102 and 204 bar and at temperatures of 99° C., 110° C., 121° C., 132° C. and 143° C. The laminates were then characterized for through thickness modulus of elasticity ($E_3$). Additionally, the modulus of a single monolayer was also measured at multiple locations.

The results are shown in Table 1. Although there is some experimental variability, $E_3$ generally increases with both increasing molding temperature and increasing molding pressure.

TABLE 1

| Pressure (bar) | Temperature (° C.) | $E_3$ (GPa) |
| --- | --- | --- |
| 10 | 99 | 0.385 |
| 10 | 110 | 0.419 |
| 10 | 121 | 2.625 |
| 10 | 132 | 0.591 |
| 10 | 143 | 3.577 |
| 103 | 99 | 1.087 |
| 103 | 110 | 2.902 |
| 103 | 121 | 2.881 |
| 103 | 132 | 3.577 |
| 103 | 143 | 4.846 |
| 207 | 99 | 0.201 |
| 207 | 110 | 1.796 |
| 207 | 121 | 3.145 |
| 207 | 132 | 3.964 |
| 207 | 143 | 4.761 |

The $E_3$ of the monolayer when tested by itself was only 0.235 GPa, with a standard deviation over five replicates of 0.007 GPa. This is surprising in view of what was found for the composite laminates, summarized in the above table, in which the $E_3$ of the molded composite laminate is much higher than the transverse modulus of the component monolayer. Depending on conditions of the article's manufacture, the $E_3$ of the reinforcement monolayer may be more than 10 or even more than 20 times lower than the composite laminate which it reinforces.

From the data of Table 1, a linear regression model ("Equation 1") of the effect of maximum molding pressure and temperature on modulus through the thickness was generated:

$$E_3 \text{ (GPa)} = -7.6731 + 0.00621283 \text{Pressure(Bar)} + 0.0781059 \text{Temperature(° C.)}$$

U.S. Pat. No. 7,972,679 and U.S. Pat. No. 7,976,932 teach that, in creating impact penetration resistant articles, pressures up to about 204 bar and temperatures up to about 127° C. are required. Equation 1 predicts then, that at most, the $E_3$ of such composite laminates would be less than 3.5 GPa. In contrast to the above findings, U.S. Pat. No. 7,972,679 teaches that such implied high $E_3$ is undesirable, stating, "The ballistic resistance of the panels generally increased as the molding temperature was decreased." Equation 1 predicts that the article made in the examples of U.S. Pat. No. 8,197,935 (noted only as molded at 40-50 bar and 130° C.) would have a $E_3$ of 2.7-2.8 GPa.

Example Series 1

The polyethylene sheet was as in the Comparative Example Series A. Each stack comprised 40 sheets. Different adhesives were used for different examples. The adhesives used were the LLDPE nonwoven PO4605 from Spunfab as previously used, an ionomeric resin dispersion, Michem® 2960, from Michelman, Cincinatti, Ohio and an ionomeric resin film, Surlyn® 8920, from DuPont. The Surlyn® film had a zero-shear-rate viscosity of 2,025,860 Pa-s at 125° C. The Michem® 2960 had a zero-shear-rate viscosity that could not be practically measured, and was estimated to be above 3,000,000 Pa-s at 125° C. based on observations of its flow. The basis weights of the adhesives are shown in Table 2. As the Michem® adhesive was supplied as a dispersion, different basis weights could be provided by coating different amounts of adhesive and allowing the adhesive to dry.

Each stack was molded to form a composite laminate as per the Comparative Examples but at varying maximum pressures and platen temperatures. It was found that the LLDPE nonwoven adhesive allowed the preforms to become unstable during pressure increase, and several parts had to be discarded due to slippage during molding. This problem was not observed with articles made from the two ionomeric adhesives, suggesting they may better enable fabrication of articles with high $E_3$.

The laminates were then subjected to a ballistic test against a 0.26-gram right circular steel cylinder projectile of approximately unit aspect ratio to determine average perforation velocity (V50), following MIL-DTL-662F, issued 18 Dec. 1997.

Table 2 summarizes the laminate compaction conditions, the resulting ballistic results and predicted $E_3$ value from the regression curve.

In every case, increasing compression temperature and pressure resulted in a higher estimated $E_3$ and enhanced ballistic performance. Regression of the data in Table 2 gives Equation 2 as:

(Kinetic Energy Absorbed at $V50$)$(J)=49.863 E_3$ $(GPa)^{0.394}, R^2=0.90$.

This surprising finding contradicts the prior teachings of U.S. Pat. No. 7,972,679, that molding at lower temperatures, pressures and corresponding lower $E_3$ is desirable for higher impact penetration resistance in a laminate. Indeed, surpassing the pressure and temperature taught previously in U.S. Pat. No. 7,972,679 gives the highest performance. It has also been found that the selection of the adhesive dictates the upper limit of $E_3$ that can be achieved.

The use of the ionomeric matrices, which are known to have high resistance to flow in the molten phase, was seen to be one practical solution to enable the manufacture of oriented polyethylene impact penetration resistant composite laminates. These laminates did not slip during molding, although the panels were molded to higher $E_3$.

Example Series 2

In a further series of examples, stacks assembled as per Example Series 1 were prepared. The adhesives used were either Michem® 2960 or Surlyn® 8920. The basis weights of the adhesives are shown in Table 3.

Each stack was molded to form a composite laminate as per the Comparative Examples but at varying maximum pressures and platen temperatures. It was found that the LLDPE nonwoven adhesive allowed the preforms to become unstable during pressure increase, and several parts had to be discarded due to slippage during molding. We did not observe this problem with articles made from the two ionomeric adhesives, suggesting they may better enable fabrication of articles with high $E_3$.

The laminates were then subjected to a ballistic test against 7.62×39 mm, 8.0 g, PS ball rounds having mild steel cores. The reported values are average values for the number of shots fired for each example. The results are shown in Table 4. The $E_3$ value is the inferred value from equation 1.

TABLE 2

| Target | Pressure Bar | Temperature (° C.) | Estimated $E_3$ (GPa) (equation 1) | Number of Cross-Plied Tapes | Plastic Matrix | Adhesive Basis Weight (gsm) | V50 m/s | Kinetic Energy Absorbed (J) |
|---|---|---|---|---|---|---|---|---|
| 1 | 203 | 99 | 1.31 | 80 | LLDPE | 6 | 658 | 56.4 |
| 2 | 203 | 99 | 1.31 | 80 | nonwoven | 6 | 666 | 57.7 |
| 3 | 203 | 99 | 1.31 | 80 | | 6 | 625 | 50.8 |
| 4 | 216 | 102 | 1.71 | 80 | | 6 | 684 | 60.8 |
| 5 | 216 | 102 | 1.71 | 80 | | 6 | 666 | 57.7 |
| 6 | 216 | 102 | 1.71 | 80 | | 6 | 698 | 63.4 |
| 7 | 136 | 121 | 2.63 | 80 | | 6 | 737 | 70.6 |
| 8 | 136 | 121 | 2.63 | 80 | | 6 | 719 | 67.2 |
| 9 | 136 | 121 | 2.63 | 80 | | 6 | 759 | 74.8 |
| 10 | 136 | 121 | 2.63 | 80 | Michelman | 3.9 | 758 | 74.7 |
| 11 | 136 | 121 | 2.63 | 80 | "Michem" | 3.9 | 780 | 79.0 |
| 12 | 136 | 121 | 2.63 | 80 | 2960 | 3.9 | 759 | 74.9 |
| 13 | 204 | 132 | 3.90 | 80 | ionomer | 3.9 | 806 | 84.4 |
| 14 | 204 | 132 | 3.90 | 80 | | 3.9 | 786 | 80.3 |
| 15 | 204 | 132 | 3.90 | 80 | | 4.4 | 819 | 87.2 |
| 16 | 204 | 132 | 3.90 | 80 | | 3.9 | 789 | 80.8 |
| 17 | 204 | 132 | 3.90 | 80 | | 3.9 | 818 | 86.9 |
| 18 | 136 | 121 | 2.63 | 80 | DuPont | 4.8 | 753 | 73.7 |
| 19 | 136 | 121 | 2.63 | 80 | Surlyn ® | 4.8 | 776 | 78.2 |
| 20 | 136 | 121 | 2.63 | 80 | 8920 | 4.8 | 779 | 79.0 |
| 21 | 204 | 132 | 3.90 | 80 | ionomer | 4.8 | 797 | 82.6 |

TABLE 3

| Sample | Manufacturing Conditions | | Inferred $E_3$ (GPa) | Matrix Resin | | |
|---|---|---|---|---|---|---|
| | Pressure (Bar) | Temperature (° C.) | | Type | Basis Weight (g/m²) | Complex Viscosity @ 125° C., 0.1-rad/s (Pa-s) |
| Comp. A | 204 | 99 | 1.3 | ethylene-octene copolymer | 6 | 1310 |
| Comp. B | 136 | 121 | 2.6 | ethylene-octene copolymer | 6 | 1310 |
| 1 | 204 | 121 | 3.1 | ethylene-octene copolymer | 6 | 1310 |
| 2 | 204 | 121 | 3.1 | ethylene-octene copolymer | 4 | 1310 |
| 3 | 204 | 121 | 3.1 | ethylene-octene copolymer | 4 | 1310 |
| 4 | 204 | 121 | 3.1 | ethylene-octene copolymer | 6 | 1793 |
| 5 | 204 | 132 | 3.9 | ethylene-octene copolymer | 6 | 1793 |
| 6 | 204 | 121 | 3.1 | ethylene-octene copolymer | 6 | 1673 |
| 7 | 204 | 132 | 3.9 | ethylene-octene copolymer | 6 | 1673 |
| 8 | 204 | 121 | 3.1 | ethylene-acrylic acid copolymer | 4.9 | 2025860 |
| 9 | 204 | 132 | 3.9 | ethylene-acrylic acid copolymer | 4.9 | 2025860 |
| 10 | 286 | 132 | 4.4 | neutralized ethylene-acrylic acid copolymer | 3.9 | believed >3000000 |

TABLE 4

| Sample | Number of Targets Tested | Did Some Panels Slip During Manufacture? | Average V50 (m/s) | Kinetic Energy Absorbed per Areal Density at V50 (J-m²/kg) | Laminate Areal Density (kg/m²) |
|---|---|---|---|---|---|
| Comp. A | 4 | no | 793 | 107 | 23.5 |
| Comp. B | 2 | yes | 896 | 149 | 21.6 |
| 1 | 5 | yes | 853 | 154 | 19.0 |
| 2 | 5 | no | 845 | 153 | 18.7 |
| 3 | 1 | no | 864 | 160 | 18.7 |
| 4 | 3 | no | 825 | 144 | 19.0 |
| 5 | 3 | no | 889 | 164 | 18.9 |
| 6 | 3 | no | 854 | 155 | 18.9 |
| 7 | 1 | no | 871 | 161 | 18.9 |
| 8 | 4 | no | 829 | 147 | 18.7 |
| 9 | 2 | no | 825 | 150 | 18.1 |
| 10 | 1 | no | 915 | 199 | 16.9 |

Several observations can be made from Tables 3 and 4. The previously unidentified property of $E_3$ correctly ranks the laminate's protective ability per weight for a given adhesive, and has more influence than the specific adhesive used. Increasing $E_3$ results in higher impact penetration resistance per weight, enabling the manufacturer to offer equally protective articles at lower weight, or more protective articles at higher weight, as long as the $E_3$ value is maintained. As the Comparative Examples show, it is possible to increase $E_3$ on materials made by the prior art of U.S. Pat. No. 7,976,932. However, many of the articles manufactured by this way shift during manufacturing, resulting in undesirable yield loss. It is possible to eliminate this problem by reducing matrix basis weight and/or by increasing adhesive zero-shear-rate viscosity near the manufacturing temperature. The combination of low adhesive basis weight, high adhesive complex viscosity, and manufacturing to high $E_3$ appears to offer the highest protection per weight; approximately double the specific kinetic energy absorbed when tested with this projectile.

What is claimed is:

1. A consolidated impact penetration resistant laminate comprising a plurality of alternating layers of (i) non-fibrous ultra-high molecular weight polyethylene monolayers and (ii) a thermoplastic adhesive, the adhesive having a basis weight of no greater than 5 gsm and a zero-shear-rate viscosity, determined from an oscillating disc rheometer in a frequency sweep between 0.1 rad/s and 100 rad/s, conducted per ASTM D 4440 at 125° C., and calculated from fitting to a Carrea-Yasuda four parameter model, of at least 10,000 Pa-s, wherein
   (a) at least 90 percent of the monolayers are arranged such that the orientation of one monolayer is offset with respect to the orientation of an adjacent monolayer, and
   (b) the modulus of elasticity through the thickness of the laminate, as measured by Test Method A, is at least 3 GPa.

2. The laminate of claim 1 wherein the modulus of elasticity through the thickness of the laminate is at least 3.2 GPa.

3. The laminate of claim 1 wherein the adhesive further comprises a thixotrope.

4. The laminate of claim 1 wherein adjacent monolayers have an orientation that is essentially orthogonal to each other.

5. The laminate of claim 2 wherein the modulus of elasticity through the thickness of the laminate is at least 3.5 GPA.

6. The laminate of claim 1 wherein the adhesive has a zero-shear-rate viscosity of at least 100,000 Pa-s.

7. The laminate of claim 5 wherein the modulus of elasticity through the thickness of the laminate is at least 4 GPa.

8. The laminate of claim 6 wherein the adhesive has a zero-shear-rate viscosity of at least 1,000,000 Pa-s.

9. The laminate of claim 3 wherein the thixotrope is an organic dendritic or inorganic particle.

* * * * *